(12) United States Patent
Noyes

(10) Patent No.: US 11,957,889 B2
(45) Date of Patent: Apr. 16, 2024

(54) ENDOSCOPIC RETRACTABLE SYRINGE DEVICE

(71) Applicant: ResnENT, LLC, Bloomington, IL (US)

(72) Inventor: Willard S. Noyes, Bloomington, IL (US)

(73) Assignee: RESNENT, LLC, Bloomington, IL (US)

( * ) Notice: Subject to any disclaimer, the term of this patent is extended or adjusted under 35 U.S.C. 154(b) by 0 days.

(21) Appl. No.: 17/707,653

(22) Filed: Mar. 29, 2022

(65) Prior Publication Data

US 2023/0310755 A1    Oct. 5, 2023

(51) Int. Cl.
| | | |
|---|---|---|
| A61M 5/32 | (2006.01) | |
| A61B 1/00 | (2006.01) | |
| A61B 1/018 | (2006.01) | |
| A61M 5/20 | (2006.01) | |
| A61M 5/315 | (2006.01) | |

(52) U.S. Cl.
CPC ....... *A61M 5/3234* (2013.01); *A61B 1/00066* (2013.01); *A61B 1/00105* (2013.01); *A61B 1/00112* (2013.01); *A61B 1/018* (2013.01); *A61M 5/2033* (2013.01); *A61M 5/31583* (2013.01); *A61M 5/3204* (2013.01)

(58) Field of Classification Search
CPC .............. A61M 5/3234; A61M 5/2033; A61M 5/31583; A61M 5/3204; A61B 1/00066; A61B 1/00105; A61B 1/00112; A61B 1/018
See application file for complete search history.

(56) References Cited

U.S. PATENT DOCUMENTS

| | | | | |
|---|---|---|---|---|
| 5,662,662 A | * | 9/1997 | Bishop | A61B 17/0684 606/139 |
| 6,165,164 A | * | 12/2000 | Hill | A61B 18/24 604/523 |
| 6,749,617 B1 | * | 6/2004 | Palasis | A61M 37/0069 606/171 |
| 9,439,829 B2 | * | 9/2016 | Lee | A61H 23/02 |
| 2002/0049414 A1 | | 4/2002 | Nobles et al. | |

(Continued)

OTHER PUBLICATIONS

International Search Report and Written Opinion mailed Jul. 12, 2023 for International Application No. PCT/US2023/016679.

*Primary Examiner* — Anh Tuan T Nguyen
*Assistant Examiner* — Rynae E Boler
(74) *Attorney, Agent, or Firm* — Sheppard, Mullin, Richter & Hampton LLP

(57) ABSTRACT

A retractable syringe device includes: a handle including a hollow body for receiving a syringe through an opening of the handle, the hollow body including a syringe actuator that moves the syringe between a distal position and a proximal position; and an instrument distally extending from the handle, the instrument including a channel extending through the instrument, the channel configured to receive a needle coupled to the syringe. When the syringe is in the distal position, a distal end of the needle distally extends from the instrument, and when the syringe is in the proximal position, the distal end of the needle is retracted into the channel. The handle of the device can include a fixed or removable structure for removably coupling to a proximal end of a shaft of an endoscope.

17 Claims, 15 Drawing Sheets

(56) References Cited

U.S. PATENT DOCUMENTS

| | | | |
|---|---|---|---|
| 2004/0260241 A1* | 12/2004 | Yamamoto | A61N 1/0575 604/117 |
| 2009/0082695 A1* | 3/2009 | Whitehead | A61B 1/00052 600/572 |
| 2014/0031740 A1 | 1/2014 | Filipi et al. | |
| 2018/0303314 A1* | 10/2018 | Noyes | A61B 1/00195 |
| 2020/0330702 A1* | 10/2020 | Wilsey | A61B 17/3478 |
| 2022/0117468 A1* | 4/2022 | Barry | A61B 1/00119 |
| 2022/0218383 A1* | 7/2022 | Barnes | A61B 17/320036 |

* cited by examiner

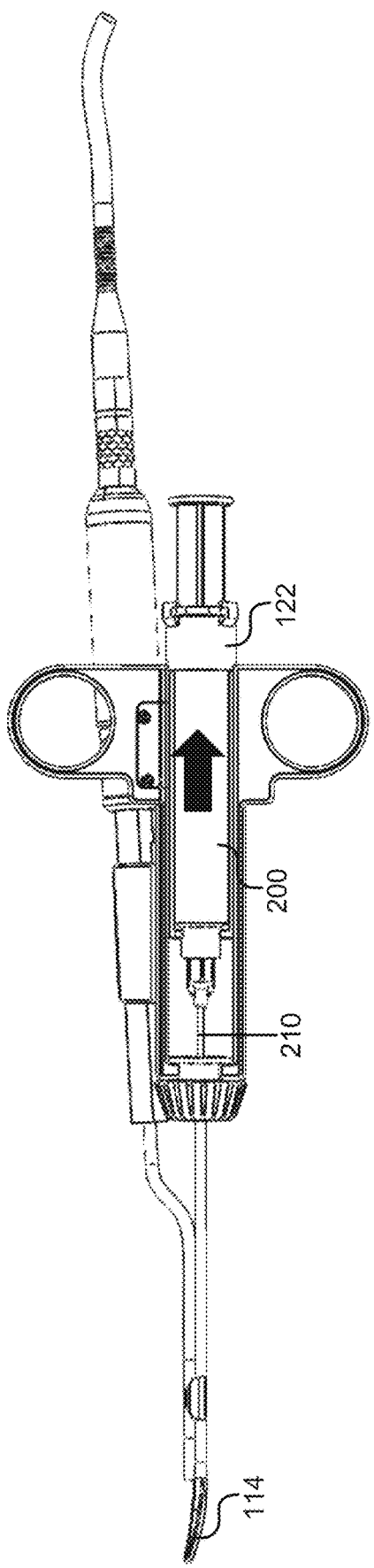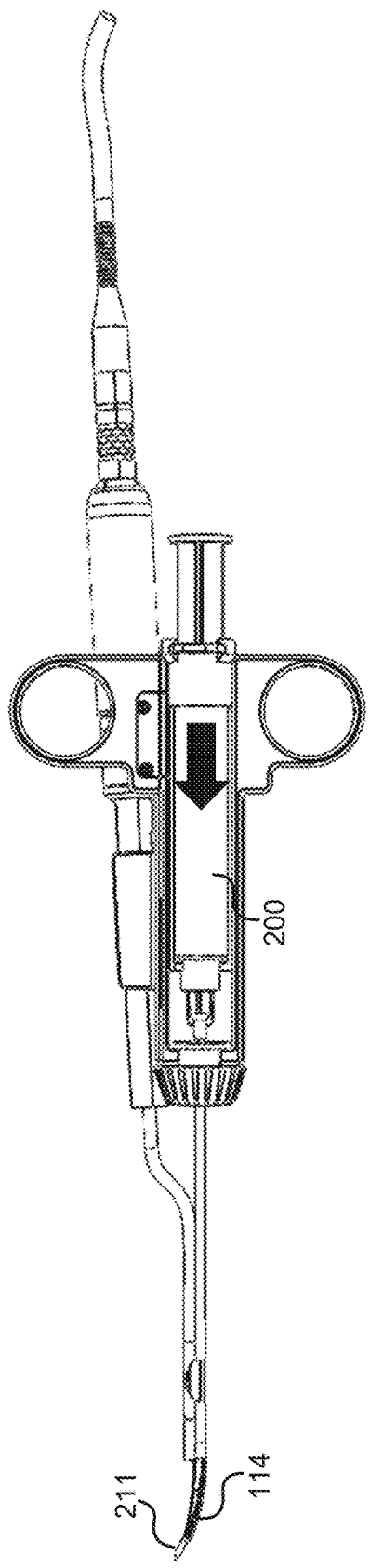
FIG. 4A
FIG. 4B

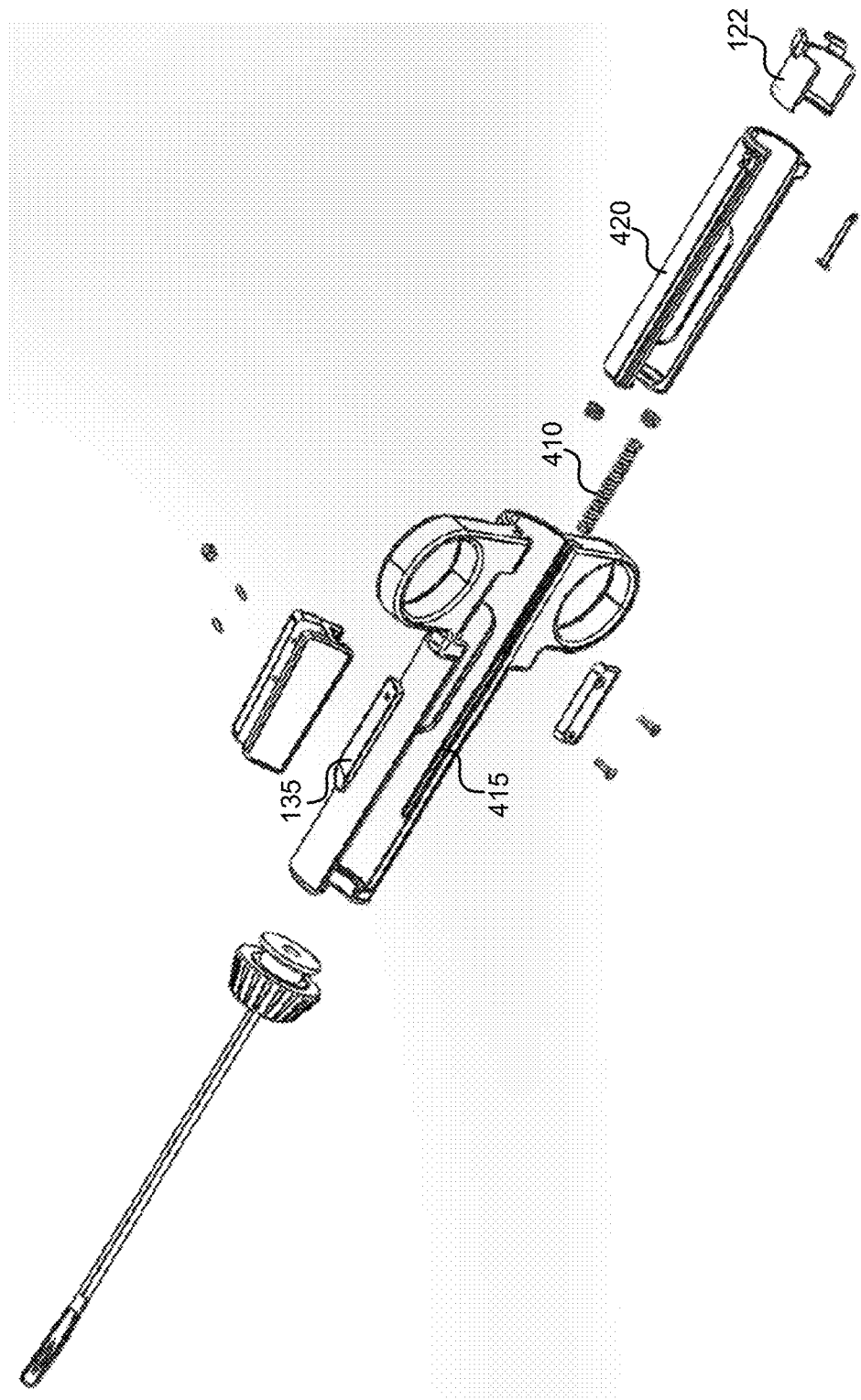

ENDOSCOPIC RETRACTABLE SYRINGE DEVICE

BACKGROUND

Endoscopes are illuminated tubular instruments with eyepieces or cameras that are used to look inside a body cavity in procedures called an endoscopy. During performance of a medical procedure with an instrument that is inserted within a patient's body cavity, endoscopes may be used to visualize the medical instrument and body cavity during the procedure. For example, the endoscope may be used to allow the physician to view tissue or other matter within a cavity or anatomic space in a patient while using suction or grasping forceps to remove tissue from the space.

In procedures that utilize medical instruments in combination with endoscopes, the endoscope is typically a rigid or flexible tool that is manipulated separately from the medical instrument. During the procedure, medical personnel hold and guide the endoscope with one hand and the instrument used to treat the patient with the other hand. Depending on the anatomic space to be visualized, physicians will use either a rigid or flexible endoscope. For example, pulmonologists and gastroenterologists use flexible endoscopes and orthopedic surgeons typically use rigid endoscopes, whereas otolaryngologists use either rigid or flexible scopes depending on the surgical application. When using endoscopes with other surgical instrumentation within a confined space, there is often interference between the endoscope and instrument when trying to manipulate within the same anatomic space. This is sometimes referred to as "sword fighting" and can make surgeries technically more difficult.

Endoscopic sinus surgery involves using endoscopes along with other instrumentation to perform surgery within the nasal passages and paranasal sinuses. This can be performed in the office or operating room either under local or general anesthesia. Endoscopic sinus surgery performed while the patient is awake can be painful and therefore typically requires some type of vasoconstriction and anesthetic whether applied topically or submucosally before or during the case. Surgeons often use a combination of topically soaked anesthetic pledgets and injectable epinephrine/lidocaine solution to achieve this goal.

Injecting local anesthetic into the paranasal sinus tissues under endoscopic guidance can be cumbersome. Smaller diameter needles such as 25-, 27- and 30-gauge needles tend to cause less bleeding and discomfort compared to larger diameter needles. This is particularly true when the patient is awake during the procedure. The disadvantage of small diameter needles is that they are flimsy and difficult to steer around intranasal structures particularly when injecting deep within the nasal cavity. For example, the needle may have to bend around a deviated nasal septum in order to inject the middle turbinate or uncinate process. The uncinate process may be obscured by an enlarged middle turbinate or concha bullosa. Depending on the degree of septal deformity, the needle may not be strong enough to resist bending. A flimsy needle may not be rigid enough to displace a structure, such as a turbinate or polyp, in order to gain access for injection into an anatomic structure farther back in the nasal passage such as the ethmoid bulla or sphenoethmoid recess. In addition, the pointed tip of the needle often inadvertently pokes the mucous membrane as it is being directed farther back into the nasal passage. This causes further bleeding and discomfort. In the end, it is often difficult to obtain adequate anesthesia and vasoconstriction because of difficulty placing the needle exactly where the anesthetic needs to be injected.

Using a thicker reinforced needle that terminates into a smaller diameter pointed tip has been utilized in an attempt to overcome this problem (STRYKER CORPORATION, ENTELLUS MEDICAL, Reinforced Anesthesia Needle, RAN 027-5). Although the needle does better at resisting bending forces, the sharp needle tip is still exposed and could still poke structures and cause bleeding during insertion. Even though the needle is reinforced, it is often inadequate to mechanically move a middle turbinate, especially turbinates with thicker bone or scarring out of the way. The small surface area of the needle pushing against the turbinate often causes the needle to indent within the tissues rather than to provide enough force to displace the structure. With this in mind, surgeons will often use an elongated, blunt, wide-tipped, curved elevator such as a Cottle elevator under endoscopic guidance to move the turbinate out of the way prior to injecting the ethmoid or sphenoid regions. In practice, this too is suboptimal because the surgeon then has to remove the elevator in order to insert the needle thereby giving time for the turbinate to fall back into its previous position and again obscure visualization. Because traditional endoscopic techniques require the surgeon to have an endoscope in one hand, only one hand remains to work the elevator or needle syringe.

SUMMARY

Some implementations described herein are directed to a retractable syringe device including an elevator configured to conceal a syringe needle until it is needed. In some implementations, an endoscope may be attached to the device to allow operation of three instruments—an elevator, syringe, and endoscope—in a single-handed manner.

In one embodiment, a retractable syringe device, comprises: a handle comprising a hollow body for receiving a syringe through an opening of the handle. In some implementations, the opening is at a proximal end of the handle and in others it is along the side of the handle. The hollow body includes a syringe actuator that moves the syringe between a distal position and a proximal position; and an instrument distally extending from the handle, the instrument including a channel extending through the instrument, the channel configured to receive a needle coupled to the syringe, wherein when the syringe is in the distal position, a distal end of the needle distally extends from the instrument, and when the syringe is in the proximal position, the distal end of the needle is retracted into the channel. In particular implementations, illustrated herein, the instrument may be a rounded, curved-tipped elevator useful for displacing anatomic structures prior to tissue injection.

In some implementations, the syringe actuator is configured to hold the syringe in place in the distal position or the proximal position.

In some implementations, the syringe actuator is configured to hold the syringe in place in multiple different distal positions where at least the distal end of the needle distally extends from the instrument in each distal position.

In some implementations, the syringe actuator comprises a spring. In some implementations, the syringe actuator further comprises a sleeve held in place by the spring, the sleeve configured to hold the syringe.

In some implementations, the handle further comprises a syringe locker that prevents removal of the syringe from the handle. In some implementations, the syringe locker comprises a twist lock mechanism. In some implementations, the syringe locker comprises a grip for holding a lip of the syringe distal to a plunger of the syringe.

In some implementations, the instrument further comprises a rotatable dial that rotates the instrument relative to the handle.

In some implementations, the handle further comprises a first fixed or removable structure for removably coupling to a proximal end of a shaft of an endoscope. In some implementations, the first fixed or removable structure for removably coupling to the proximal end of the shaft of the endoscope comprises a magnetic attachment, a snap on attachment, a top-down ratchet attachment, an insert ratchet attachment, or an insert twist attachment.

In some implementations, the instrument further comprises a second fixed or removable structure for removably coupling to a distal end of the shaft of the endoscope. In some implementations, the second fixed or removable structure for removably coupling to the distal end of the shaft of the endoscope comprises: a magnetic attachment, a loop, a clip, an elongated tube, or a removable insert.

In some implementations, the handle further comprises a handgrip.

In some implementations, the handle comprises an elevated surface; the first structure comprises an open channel configured to be removably coupled to the elevated surface; and the open channel comprises a depressible tab configured to be depressed into an opening of the elevated surface when the proximal end of the shaft of the endoscope is removably coupled to the first structure.

In one embodiment, a retractable syringe device assembly, includes: a syringe including a reservoir for storing fluid; a needle to couple to the syringe and inject the fluid at an anatomical site; handle including a hollow body for receiving the syringe through an opening of the handle, the hollow body including a syringe actuator that moves the syringe between a first position and a second position; and an instrument distally extending from the handle, the instrument including a channel extending through the instrument, the channel configured to receive the needle, where when the syringe is in the distal position, a distal end of the needle distally extends from the instrument, and when the syringe is in the proximal position, the distal end of the needle is retracted into the channel.

In some implementations, the assembly further comprises the endoscope, and the handle includes a structure for removably coupling to a proximal end of a shaft of the endoscope.

Other features and aspects of the disclosed technology will become apparent from the following detailed description, taken in conjunction with the accompanying drawings, which illustrate, by way of example, the features in accordance with implementations of the disclosed technology. The summary is not intended to limit the scope of any inventions described herein, which are defined by the claims and equivalents.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The present disclosure, in accordance with one or more implementations, is described in detail with reference to the following figures. The figures are provided for purposes of illustration only and merely depict example implementations. Furthermore, it should be noted that for clarity and ease of illustration, the elements in the figures have not necessarily been drawn to scale.

Some of the figures included herein illustrate various implementations of the disclosed technology from different viewing angles. Although the accompanying descriptive text may refer to such views as "top," "bottom" or "side" views, such references are merely descriptive and do not imply or require that the disclosed technology be implemented or used in a particular spatial orientation unless explicitly stated otherwise.

FIG. 4A shows a left side view of a retractable syringe device with mounted syringe and endoscope, when the syringe is in a proximal position within the retractable syringe device body, in accordance with some implementations of the disclosure.

FIG. 4B shows the retractable syringe device of FIG. 4A when the syringe is in a distal position within the device body.

FIG. 5 shows an exploded view of a retractable syringe device including a syringe actuating mechanism, in accordance with some implementations of the disclosure.

Figure 1A:
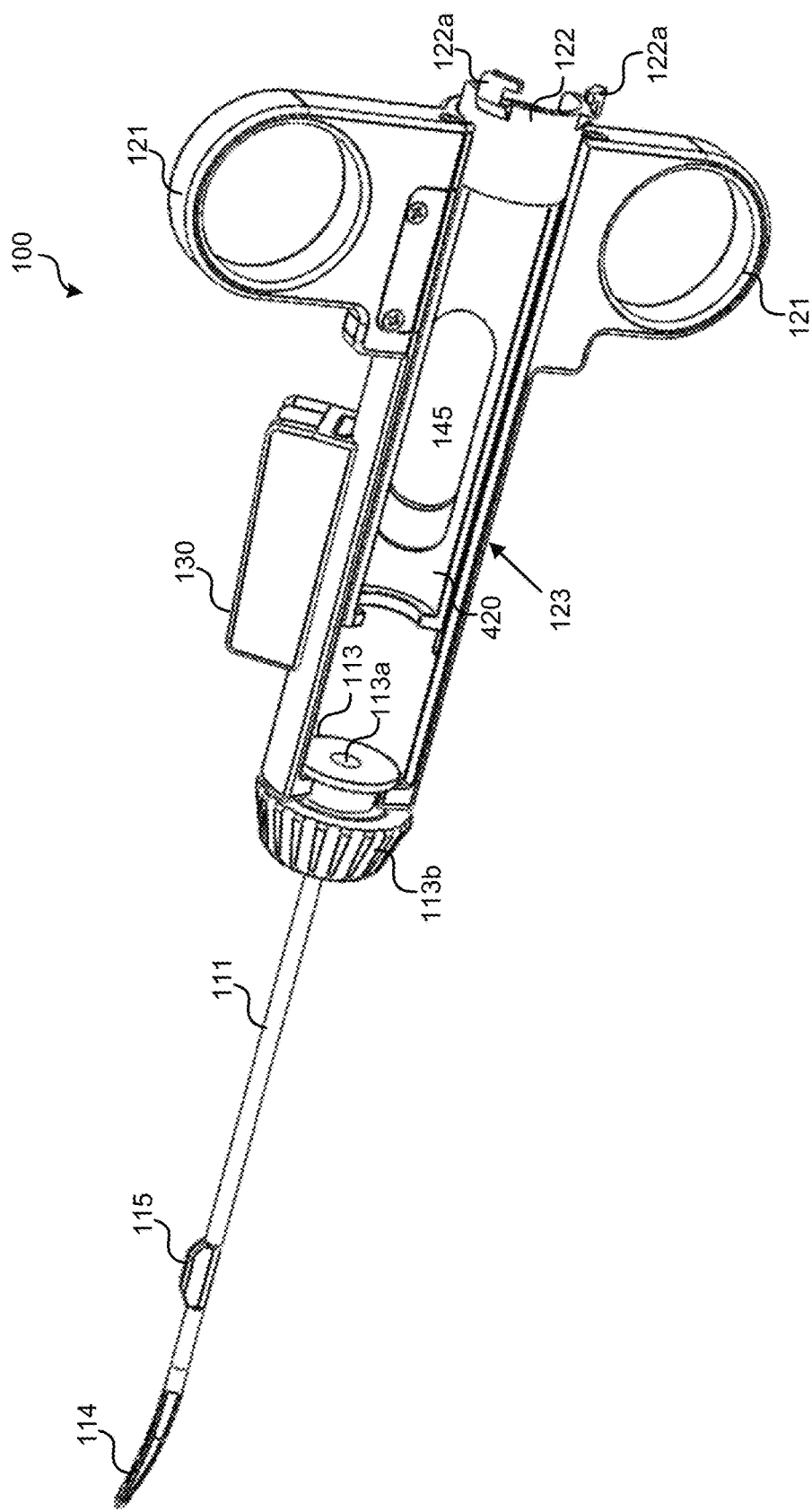
FIG. 1A shows a perspective, left side view of a retractable syringe device, in accordance with some implementations of the disclosure.
Figure 1B:
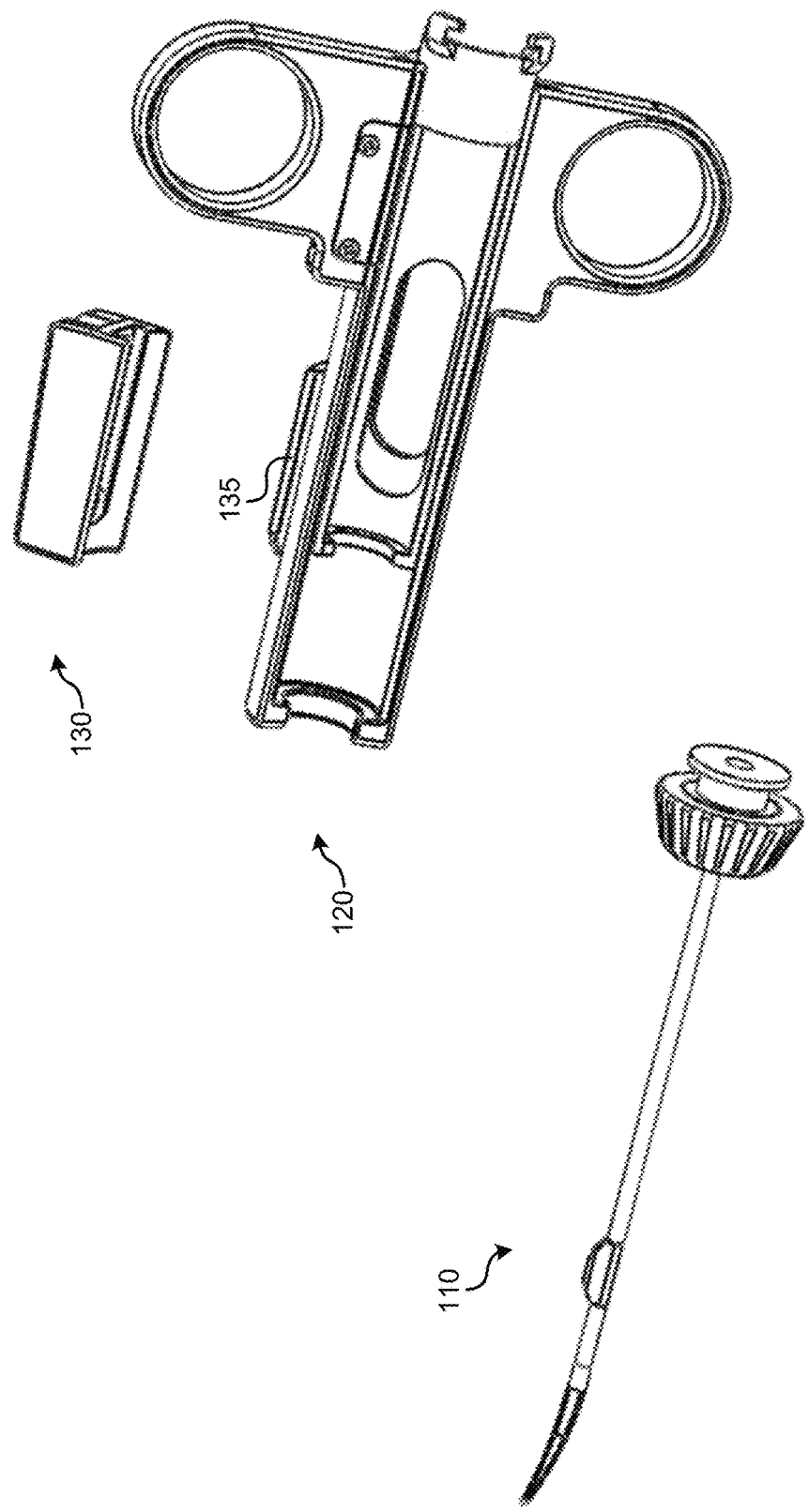
FIG. 1B shows an exploded view of the retractable syringe device of FIG. 1A.
Figure 1C:
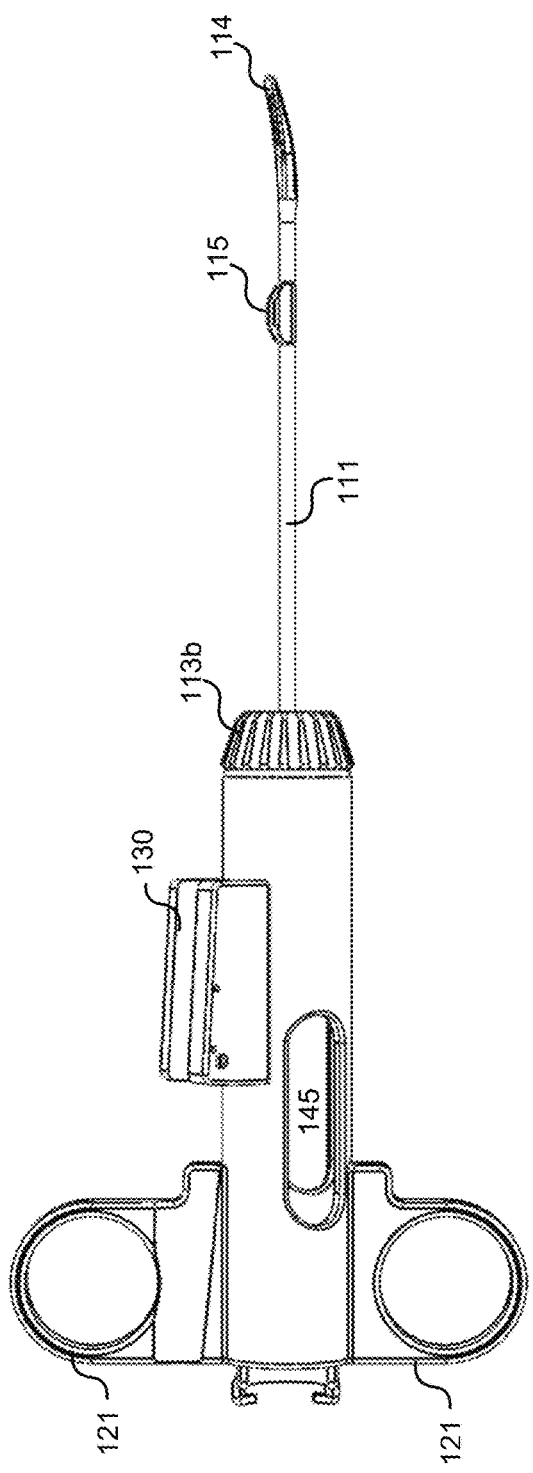
FIG. 1C shows a right side view of the retractable syringe device of FIG. 1A.
Figure 1D:
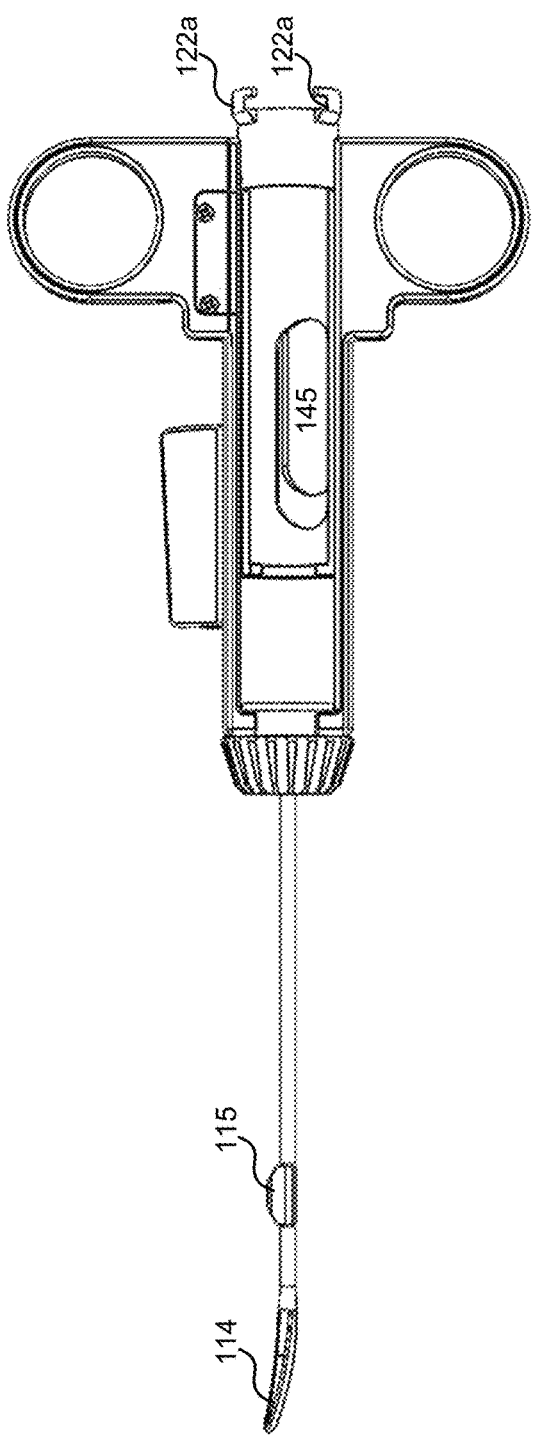
FIG. 1D shows a left side view of the retractable syringe device of FIG. 1A.
Figure 1F:
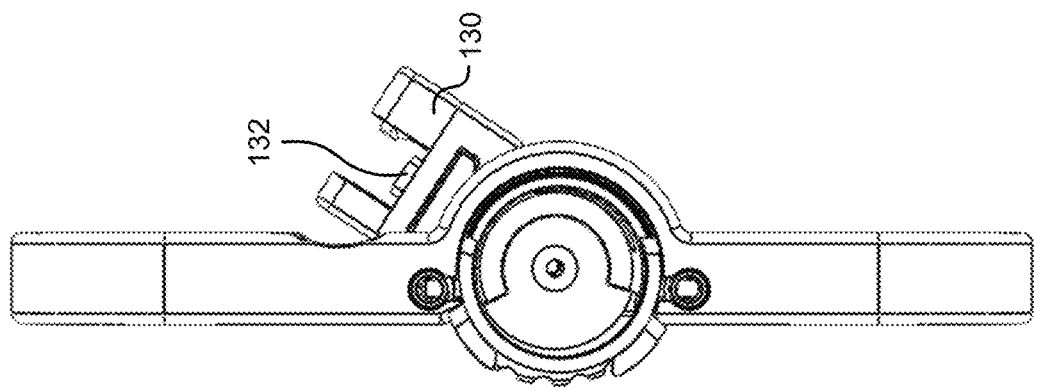
FIG. 1F shows a rear side view of the retractable syringe device of FIG. 1A.
Figure 1E:
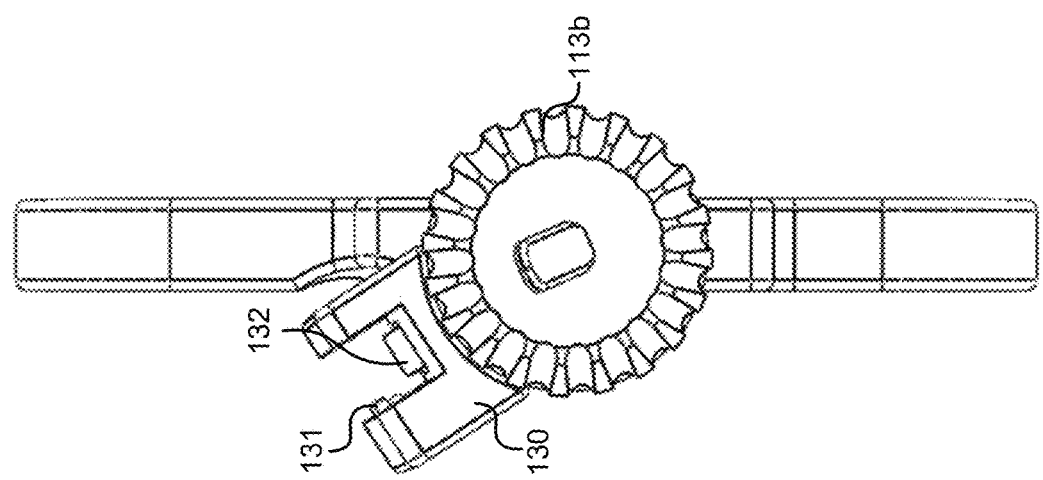
FIG. 1E shows a front side view of the retractable syringe device of FIG. 1A.
Figure 2A:
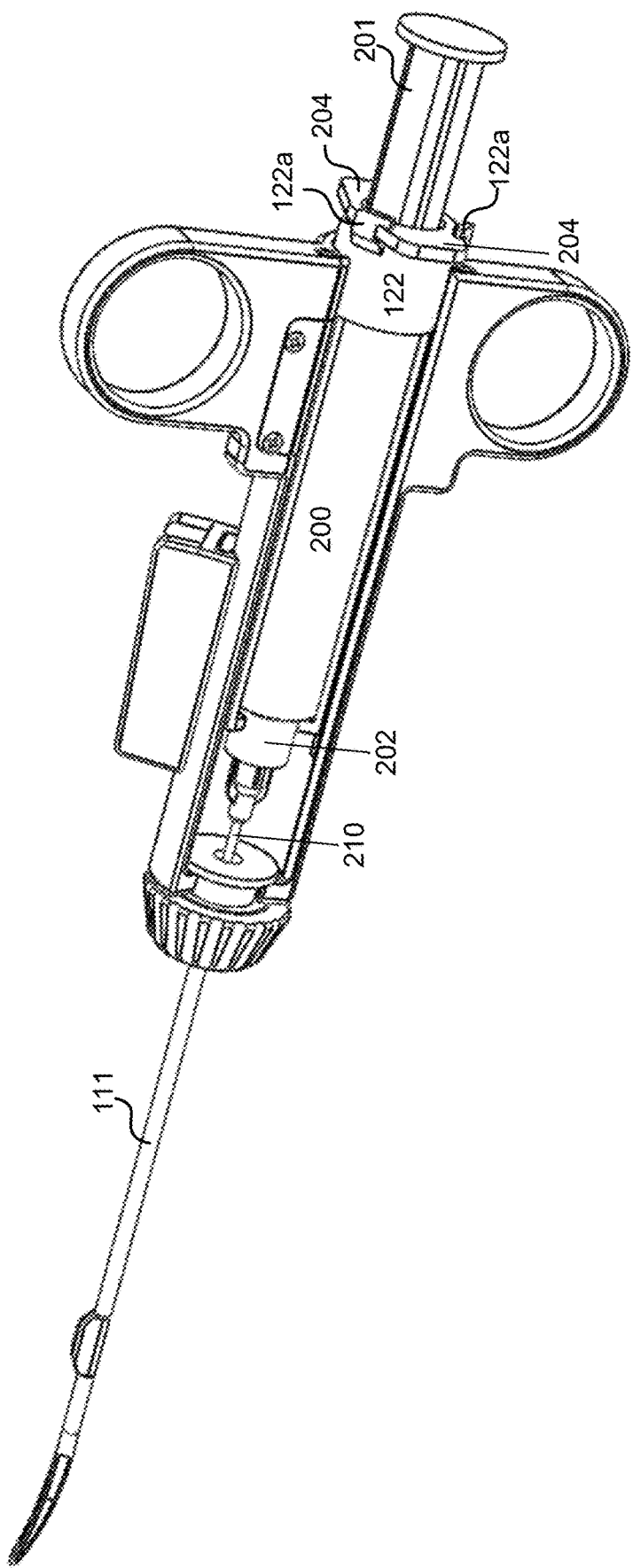
FIG. 2A shows a perspective, left side view of the retractable syringe device of FIG. 1A with a syringe mounted therein, in accordance with some implementations of the disclosure.
Figure 2B:
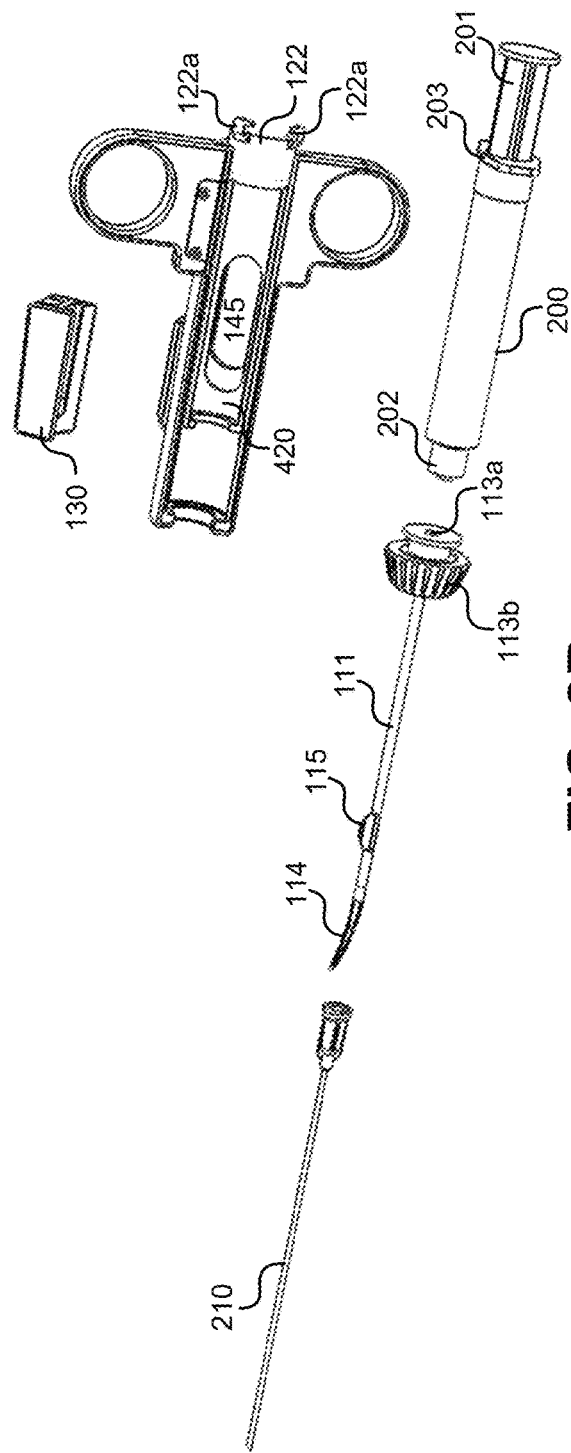
FIG. 2B shows an exploded view of the retractable syringe device and syringe of FIG. 2A.
Figure 2C:
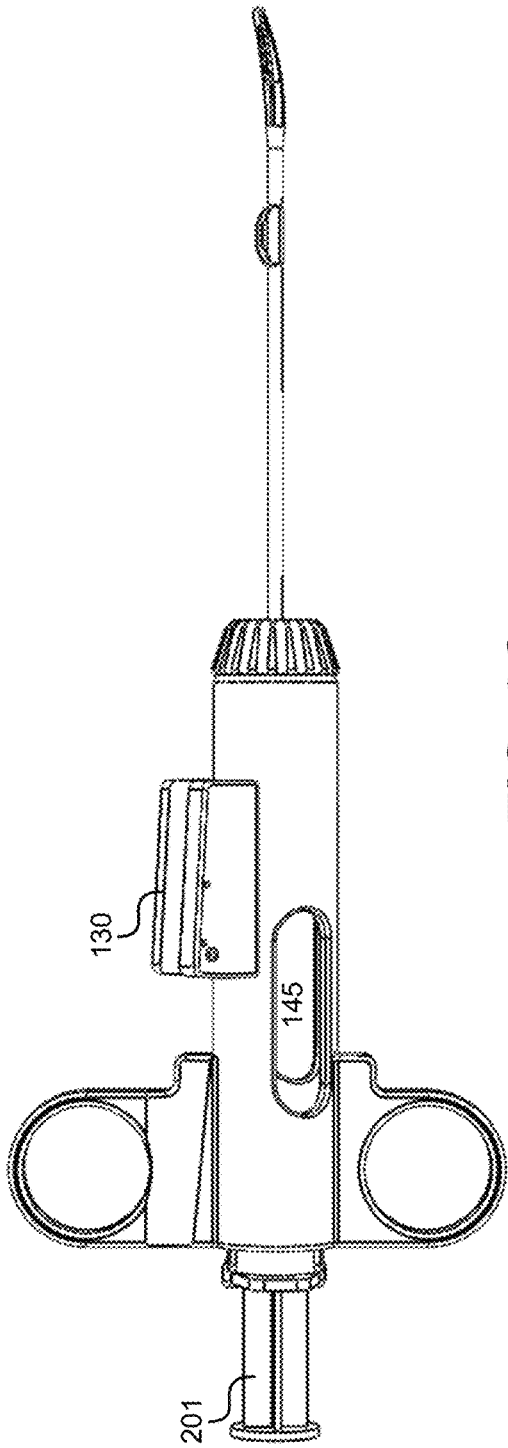
FIG. 2C shows a right side view of the retractable syringe device with mounted syringe of FIG. 2A.
Figure 2E:
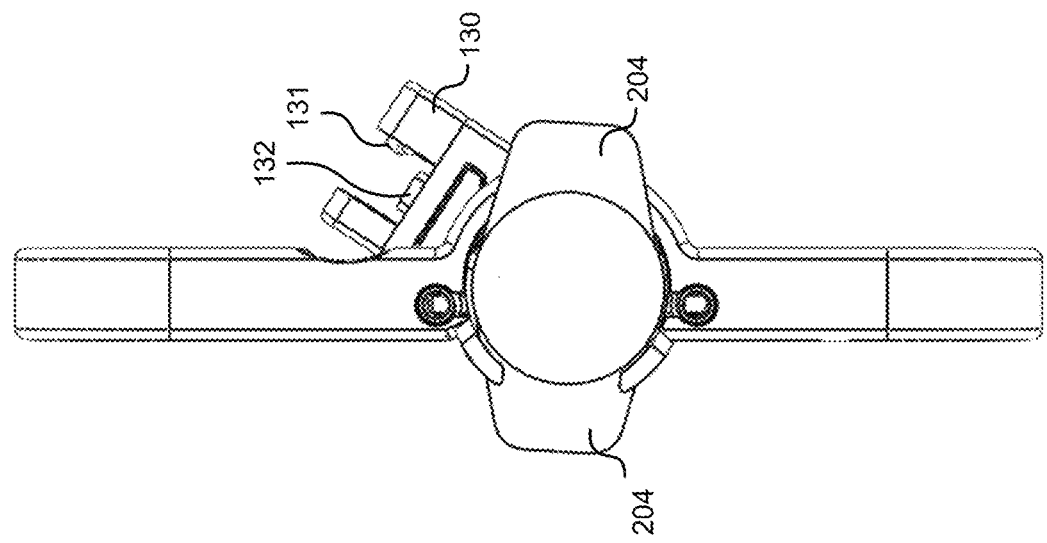
FIG. 2E shows a rear side view of retractable syringe device with mounted syringe of FIG. 2A.
Figure 2D:
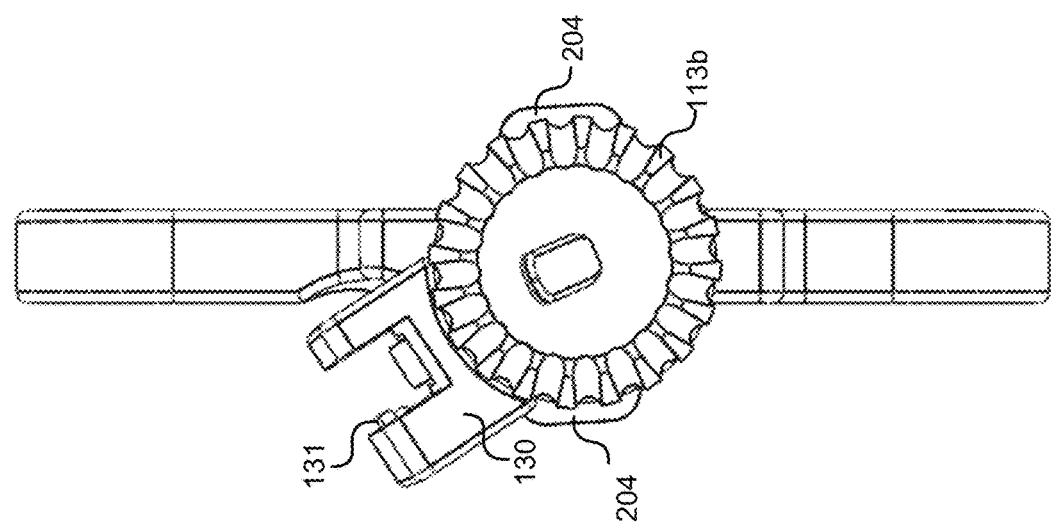
FIG. 2D shows a front side view of retractable syringe device with mounted syringe of FIG. 2A.
Figure 3A:
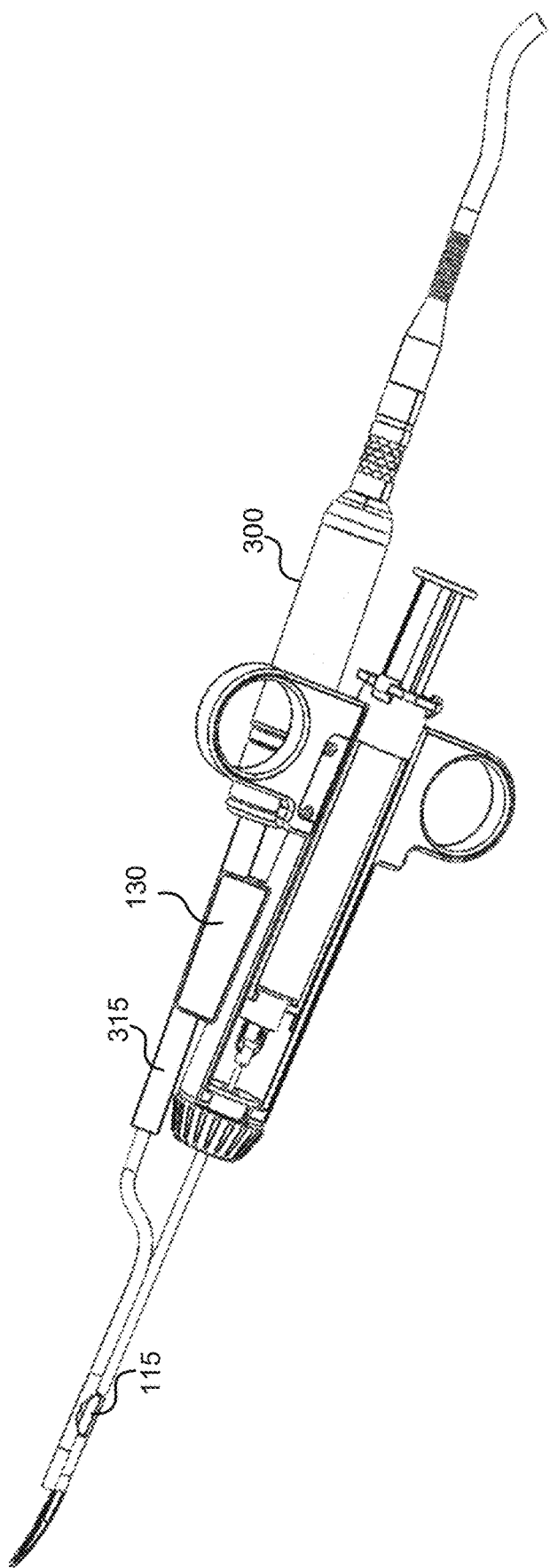
FIG. 3A shows a perspective side view of the retractable syringe device of FIG. 1A with a syringe mounted therein and an endoscope removably coupled thereon, in accordance with some implementations of the disclosure.
Figure 3B:
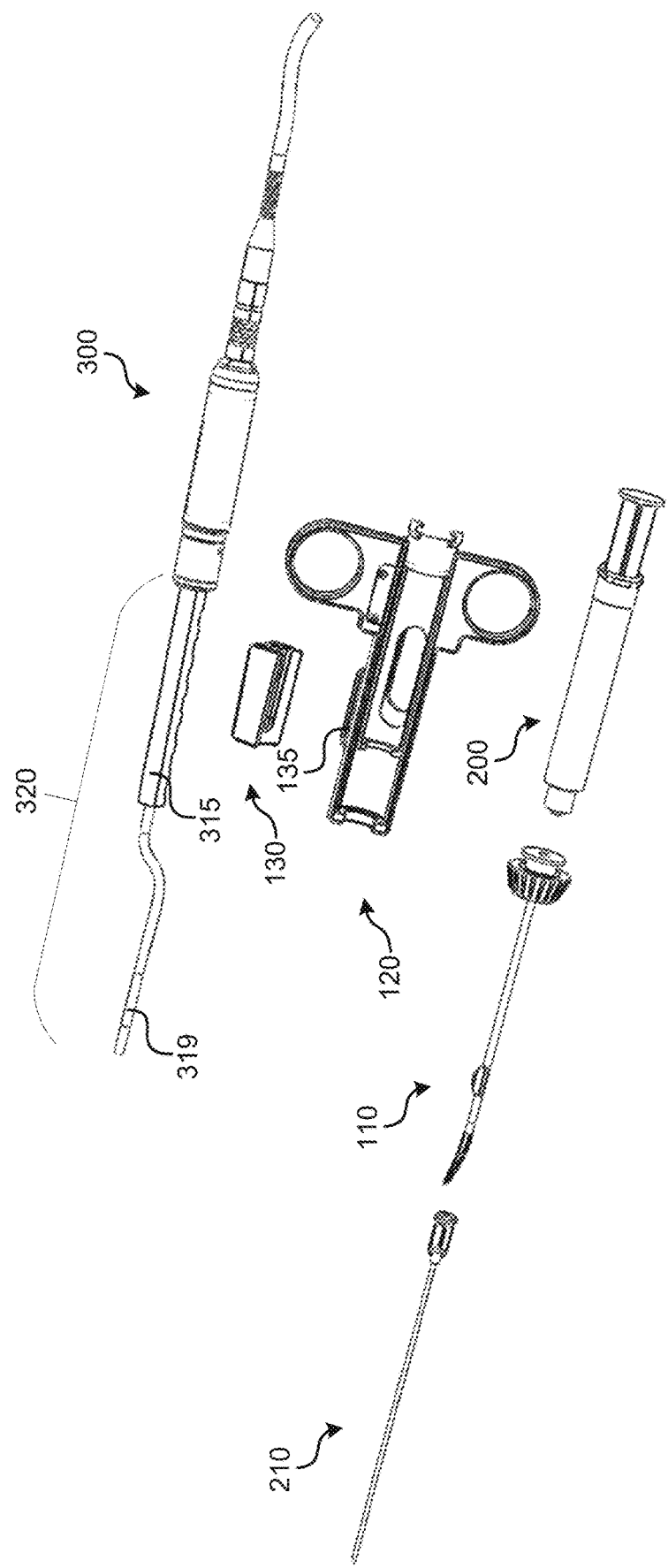
FIG. 3B shows an exploded view of the retractable syringe device, syringe, and endoscope of FIG. 3A.
Figure 3C:
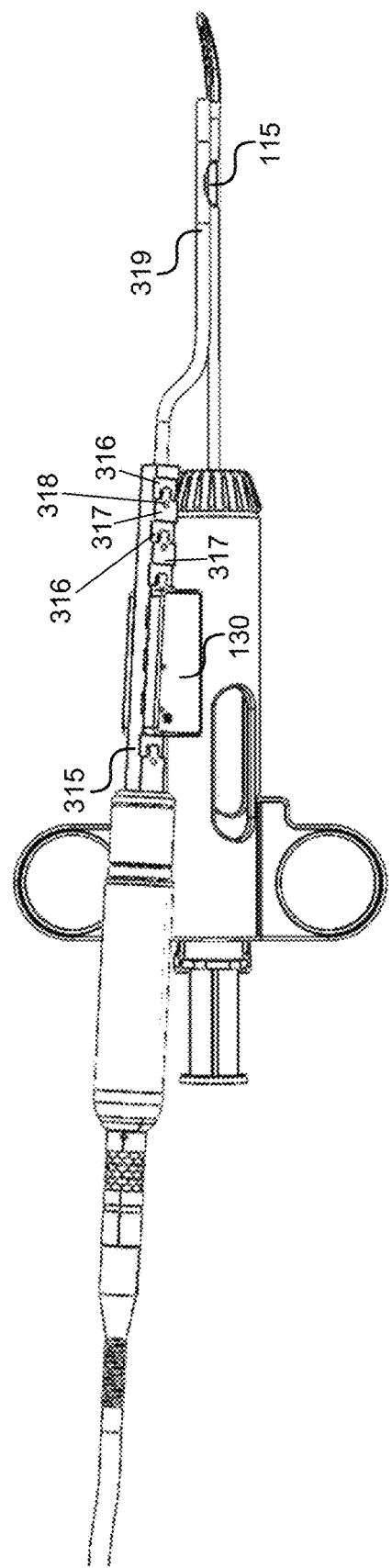
FIG. 3C shows a right side view of the retractable syringe device with mounted syringe and endoscope of FIG. 3A.
Figure 3D:
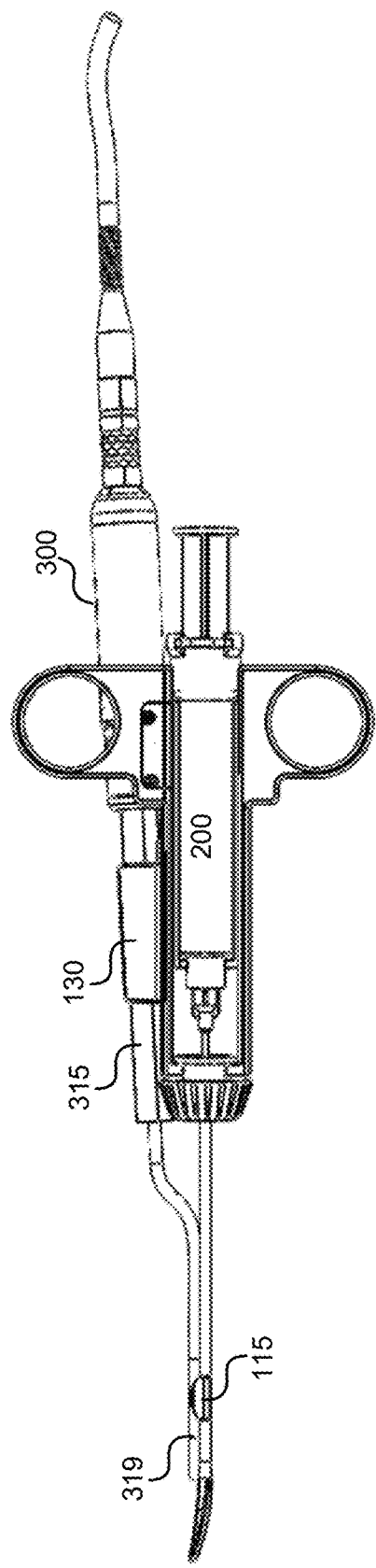
FIG. 3D shows a left side view of the retractable syringe device with mounted syringe and endoscope of FIG. 3A.
Figure 3F:
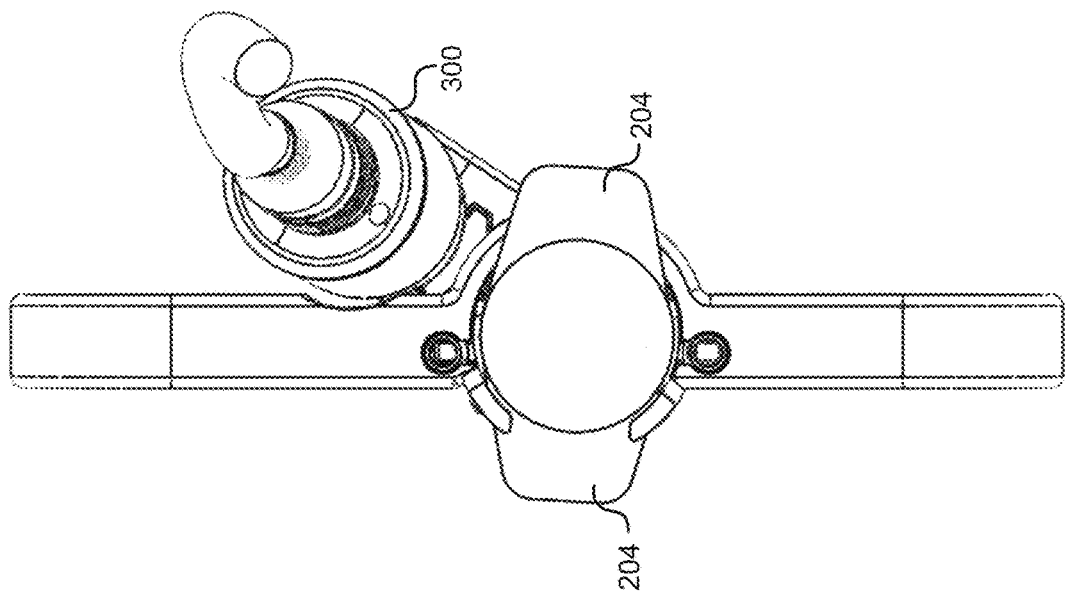
FIG. 3F shows a rear side view of the retractable syringe device with mounted syringe and endoscope of FIG. 3A.
Figure 3E:
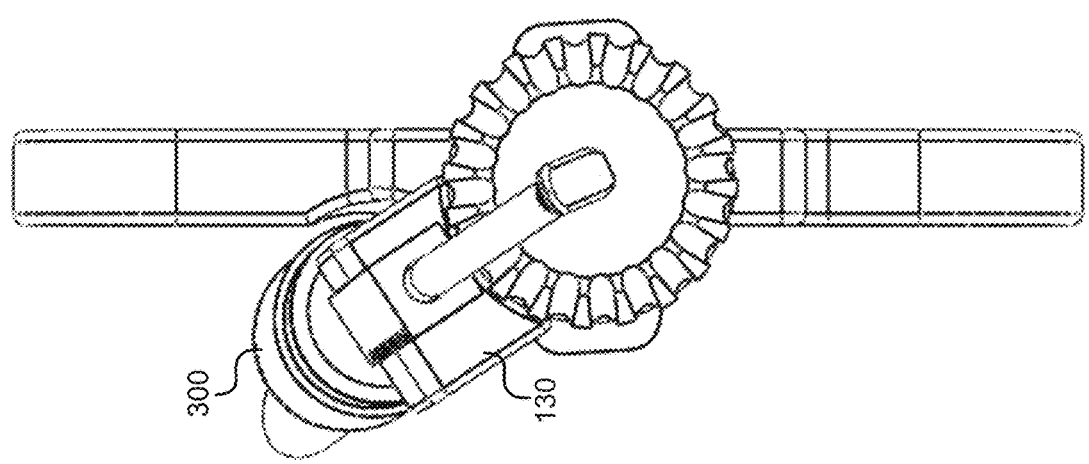
FIG. 3E shows a front side view of the retractable syringe device with mounted syringe and endoscope of FIG. 3A.

The figures are not exhaustive and do not limit the present disclosure to the precise form disclosed.

DETAILED DESCRIPTION OF THE EMBODIMENTS

The disclosure describes a system and method to combine a needle and medical instrument into one device. To this end, implementations of the disclosure are directed to a retractable syringe device including an elevator configured to conceal a needle until such time as proper visualization and localization of the needle is assured. Once the sharp needle is ready for injection, it may be advanced through a distal end of the elevator. After use, the needle may be retracted into the elevator. Further implementations of disclosure are directed to an endoscopic retractable syringe device that allows for an endoscope to be attached to the elevator/needle assembly in a single-handed manner.

In implementing some of the embodiments described herein, a surgeon may control three devices easily with one hand (endoscope, elevator, and syringe needle), thereby freeing up the other hand to control a fourth instrument such as a suction or forceps simultaneously. In this manner, the surgeon may have four devices in the nose (or other anatomical location) at one time compared to the traditional technique where they only can use two (endoscope and syringe needle). These and other advantages are further described below.

FIGS. 1A-3F depict a retractable syringe device 100, in accordance with some implementations of the disclosure. FIGS. 1A-1F show the retractable syringe device 100 without a syringe. FIGS. 2A-2E show the retractable syringe device 100 with a syringe 200 mounted therein. FIGS. 3A-3F show the retractable syringe device 100 with a syringe 200 mounted therein and an endoscope 300 removably coupled to device 100. The depicted assembly including retractable syringe device 100 may be utilized in various endoscopic applications that require injection of a fluid such as anesthetic, including applications involving the sinus, trachea, esophagus or other such applications.

The retractable syringe device 100 includes an elevator 110 and handle 120. Each of the elevator 110 and/or handle 120 may be disposable and/or reusable.

Handle 120 includes a handgrip 121, and a hollow body for receiving a syringe 200 with a needle 210 through an opening at a proximal end of handle 120. The body of handle 120 includes a syringe locking mechanism 122 to prevent removal of the syringe from handle 120. It also includes a syringe actuating mechanism 123 that actuates syringe 200 forward or backward. As depicted, the syringe actuating mechanism 123 may include a sleeve 420 for holding the syringe 200. Although handgrip 121 is depicted as having two fingerholes, other handgrip mechanisms and conformities may be used with handle 120.

Elevator 110 extends from a distal end of handle 120, and it includes a proximal end 113, a shaft 111, and a distal end 114. The distal end 114 may have a curved elevator tip that is blunt. The distal end 114 may be a rigid or semi-rigid structure configured to move or otherwise manipulate tissue (e.g., prior to injection with a needle 210). This may facilitate endoscopic visualization of an anatomical site prior to injection with the needle. Shaft 111 of elevator 110 includes an elongated channel running through its length. In some implementations, the elevator may be removably coupled to the distal end of handle 120. For example, proximal end 113 may be pressure or snap fitted into an opening at the distal end of handle 120. In other implementations, elevator 110 may not be removable. For example, elevator 110 may be integrated into the distal end of handle 120. In one embodiment, once attached to the handle, a proximal elevator dial 113b could rotate 180-360 degrees along its long axis.

Prior to use of retractable syringe device 100, a syringe 200 is prepared by filling its reservoir with fluid (e.g., anesthetic). For example, after forming a vacuum with a vial of fluid, a needle 210 coupled to a distal end 202 of syringe 200 may receive the fluid by pulling back plunger 201 of syringe 200. Depending on the application, the syringe could contain fluids other than anesthetic. For example, the syringe may be filled with an irrigation fluid that is dispensed by the needle during a procedure.

Once the syringe 200 is prepared, an operator (e.g., surgeon) may insert the syringe 200 into an opening of the hollow body of handle 120. In the illustrated implementation, the syringe 200 may be inserted through the opening at the proximal end of handle 120 or by snapping or otherwise inserting it into the side of handle 120, but other insertion configurations may be utilized. The syringe 200 may be inserted until a lip 203 of the syringe distal to the end of plunger 201 contacts syringe locking mechanism 122. The syringe 200 may be locked into place by rotating the assembly such that arms 204 of lip 203 contact grips of 122a of syringe locking mechanism 122. In other embodiments, the arms 204 may snap into the contact grips of 122a of syringe locking mechanism 122. Once locked into place, this may prevent removal of syringe 200 from handle 200. To unlock and permit removal of the syringe 200, the assembly maybe be rotated in the opposite direction such that the arms 204 and grips 122a no longer are in contact. An opening 145 in the body of handle 120 may facilitate an operator with pushing syringe 200 in or out of handle 120. Although a twist lock mechanism is depicted in this example, other mechanisms may be utilized to secure syringe 200 into handle 120 and syringe arms 204 into the syringe locking mechanism 122 such that it does not move laterally during an operation.

During insertion of syringe 200 in handle 120, needle 210 may be inserted into the channel of shaft 111 of elevator 110 via a first opening 113a at proximal end 113. The distal end of the needle 210 may be advanced through a second opening of distal end 114 when it is used to inject an anatomical site. During operation of device 100, the sharp tip of needle 210 may be concealed within elevator 110 until such time as proper visualization and distal localization of the needle 210 is assured. Once all obstructing structures are moved out of the way with the elevator 110 and line of sight established, the syringe needle 210 may be advanced through the elevator tip to expose the needle 210 and inject the tissue by pressing plunger 201. Once the injection is complete, the needle 210 may be withdrawn into the tip of the elevator until the next site is exposed after which the needle can be advanced again. In this manner, the needle tip is prevented from poking other areas during repositioning and bleeding is minimized.

In some implementations, rather than injecting an anatomical site with a fluid, the needle 210 of syringe 200 may instead be utilized to extract fluid or other matter from an anatomical site. The extracted fluid may be stored in the reservoir of syringe 200 for subsequent examination.

During operation, actuating mechanism 123 is configured to move syringe 200 forward or backward within the hollow body of handle 120. This mechanism is illustrated by FIGS. 4A-4B, which show left side views of a retractable syringe device when the syringe 200 is in a proximal position (FIG. 4A) and a distal position (FIG. 4B) within the body of the handle 120. As depicted by FIG. 4B, when the syringe 200 is advanced forward to a forward position, the coupled syringe needle 210 also advances forward, and at least the distal end 211 of the syringe needle 210 extends from the distal end 114 of the elevator 110. As depicted by FIG. 4A, the syringe 200 is moved back from the forward position, the coupled syringe needle 210 also moves back, and the distal end 211 of syringe needle 210 is retracted into the channel of shaft 111.

To facilitate operation, actuating mechanism 123 may be configured to extend or retract the syringe needle 210 through the distal end 114 of elevator 110 in a "pen-click" matter. In particular, actuating mechanism 123 may lock or otherwise hold the syringe 200 in place after it is moved from the retracted position to the extended position, or from the extended position to the retracted position. In this manner, an operator of retractable syringe device 100 does not need to manually hold the syringe 200 in a particular position, and the ergonomics of device 100 are improved. To retract or extend the syringe needle 210, the actuating mechanism may incorporate a control (e.g., button, slider, trigger, dial, etc.) that may be actuated (e.g., pressed, slid, pulled, turned, or otherwise manipulated) by an operator of device 100 to move the syringe forward or backward within the body of the handle 120.

In one implementation, illustrated by FIG. 5, to enable movement and locking of the syringe 200 between different positions, the actuating mechanism 123 includes a spring-loaded sleeve incorporated into the body of handle 120. The spring-loaded sleeve includes a sleeve 420 that can hold a syringe 200, and a spring 410 within a channel 415 in an interior of handle 120. In this implementation, the syringe locking mechanism 122 may be attached to sleeve 420 (e.g., at a proximal end of the sleeve 420). The spring 410 may provide tension required to retract sleeve 420. The spring may be held in place by a lock screw. The spring may hold the sleeve 420 in place, as may the lock screw. In some implementations, the mechanism includes one or more cams to hold the sleeve in each position. In such implementations, the spring 410 may also provide the tension and recoil necessary to work a pawl and cam mechanism.

Figure 6:
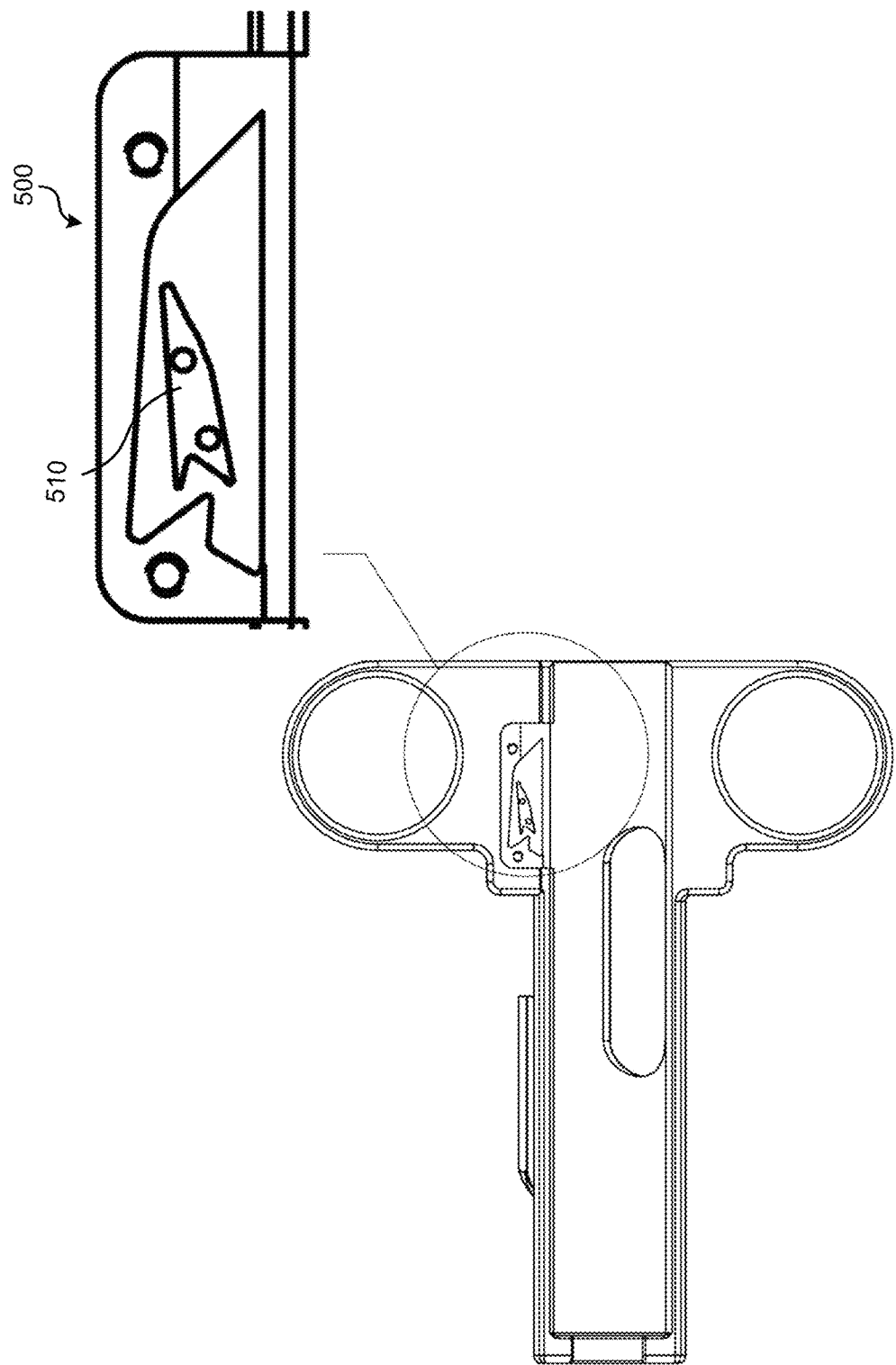
FIG. 6 shows a right side view of a retractable syringe device including a syringe actuating mechanism with a cam track, in accordance with some implementations of the disclosure.
Figure 7:
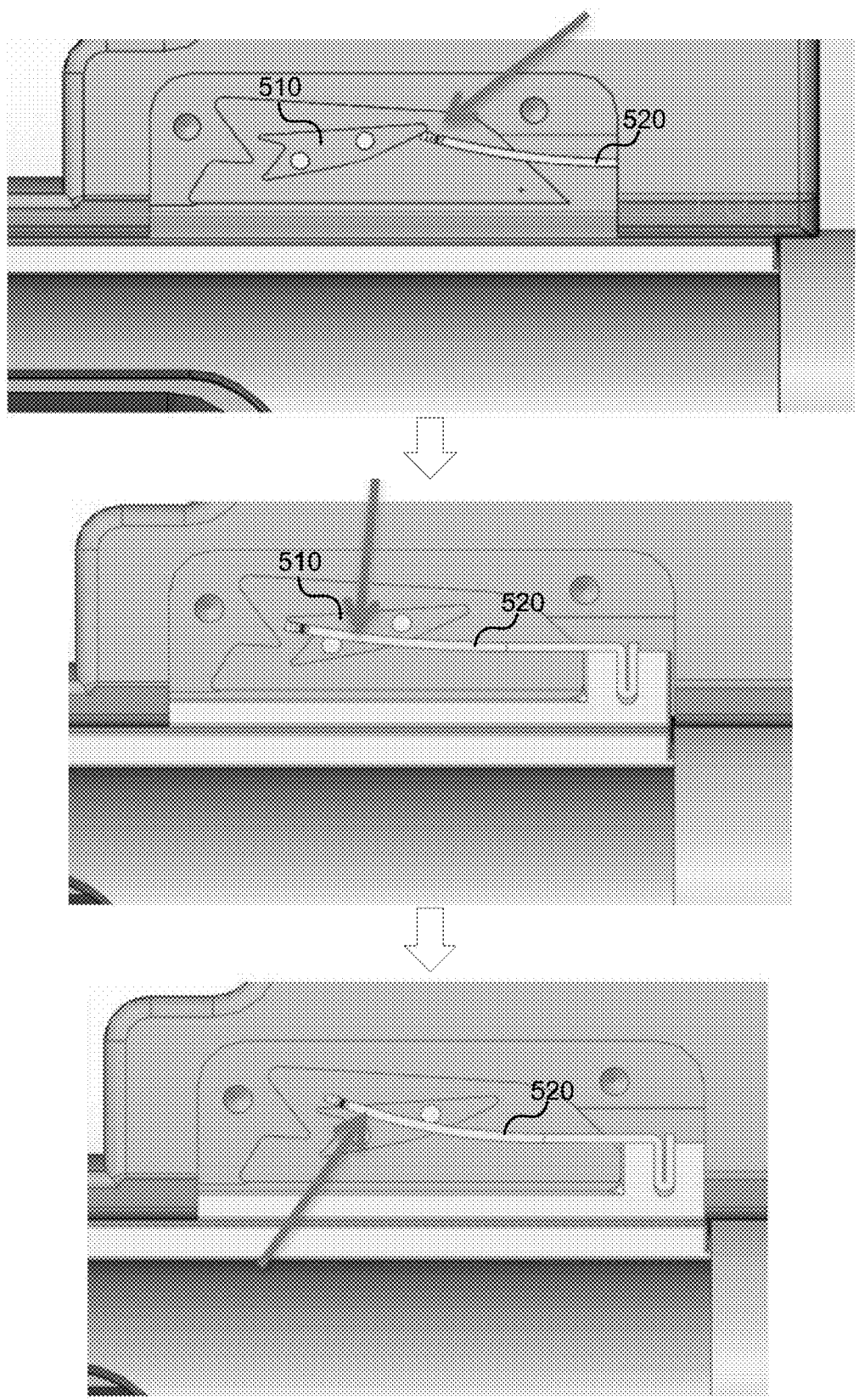
FIG. 7 shows the operation of a cam track mechanism of a retractable syringe device during extension and retraction of a syringe, in accordance with some implementations of the disclosure.

FIGS. 6-7 illustrate an example cam track mechanism 500 that may be incorporated into an actuating mechanism 123 of a handle 120, in accordance with some implementations of the disclosure. The cam track mechanism 500 includes a cam 510 and a pawl 520. FIG. 7 depicts the path the pawl 520 takes during extension and retraction. When the syringe 200 is in handle 120, it may be pushed/slid forward to engage pawl 520 the front of cam 510 and hold the assembly in an extension position. To retract the assembly, the syringe may be pushed again, causing pawl 520 to disengage and move over the top of cam 510.

Other mechanisms for retracting and extending the syringe than described herein may be utilized with the retractable syringe device 100. For example, in some implementations it is envisioned that the needle 210 could be extended or withdrawn in a stepwise fashion to allow for greater or lesser needle extension beyond the channel of shaft 111. In such implementations, the syringe 200 could shift between at least three different positions within the handle body, including: a fully extended position (e.g., syringe placed at most distal position possible within handle body such that needle is at maximum extension from channel), a partially extended position (e.g., syringe placed at an intermediate position within the handle body such that the needle partially extends from channel), and a retracted position (e.g., syringe placed at distal position within the handle body such that the distal end of needle is in the channel).

The location of the "pen-click" mechanism described above may vary. It may be contained anywhere within the handle, either proximally or distally, or contained within a separate cartridge and reversibly attachable to the syringe, needle, and/or to the device handle.

As also depicted in the figures, proximal end 113 of elevator 110 may include a rotatable dial 113b that permits rotation of elevator 110 relative to handle 120. The rotatable dial 113b may be rotated in stepwise or continuously through 360 degrees. For example, depending on the desired number possible circumferential positional adjustments, it may be configured to rotate in stepwise increments of 10°, 15°, 20°, 30°, 40°, 45°, 60°, 72°, 90°, 120°, or 180°. This may improve the ergonomics the assembly, enabling repositioning of elevator 110 (and needle 210) as needed, and also enabling repositioning of an endoscope 300 in embodiments where it is coupled to retractable syringe device 100.

As further depicted in the figures, the retractable syringe device 100 includes structures for removably coupling an endoscope 300 to device 100. In this implementation, a surface of the body of handle 120 includes an open channel 130 configured to receive a rigid attachment segment 315 located at a proximal end of the shaft 320 of endoscope 300. On the surface of one of the sides of segment 315 are formed a plurality of grooves/slots 316 and a plurality of sections 317 that protrude relative to the grooves 316, each of the sections 317 having a recessed indentation or hole 318. In this example, the plurality of grooves 316 and the plurality of sections 317 alternate along the longitudinal length of segment 130. At least one groove 316 and at least one section 317 (e.g., a groove 316 adjacent a section 317) may be used to couple the segment 315 to channel 130 of retractable syringe device 100 in a specific lengthwise position. In this manner, the endoscope 300 may be coupled to channel 130 in a specific lengthwise position. The number of grooves 316 and the number of sections 317 may depend on the desired number of lengthwise adjustments for coupling endoscope 300 to device 100, and the increment of each lengthwise adjustment. The number of grooves 316 and number of sections 317 may also depend on the width of each groove 316 and the width of each section 317.

In this implementation, the coupling mechanism between channel 130 and segment 315 uses a top-down ratchet mechanism. Rigid attachment segment 315 may be secured in place by i) pushing it down into open channel 130 along openings of two adjacent grooves 316; and ii) sliding rigid attachment segment 315 relative to open channel 130 to position each ridge 131 of channel 130 within a respective groove 316 of the adjacent grooves 316 such that protruding portions of sections 317 adjacent the grooves 316 prevent lifting of the rigid attachment segment 315 (i.e., they block the ridges 131). Additionally, when the assembly is slid, a spring-loaded protrusion (not shown) within channel 130 may be secured within an indentation/hole 318 of the section 317 positioned between the two grooves 316. To reposition rigid attachment segment 315 at a different lengthwise position, the above-described operations may be reversed (i.e., it may be slid out of place, lifted off, and secured along other grooves 316).

In the illustrated embodiments, channel 130 is configured as a slide-on channel adapter that slides onto an elevated surface or rail 135 of the body of handle 120, forming a removable connection. Also depicted in the figures is a depressible tab 132 on the bottom of channel 130. Depressible tab 132 is configured to be pushed down into an opening of elevated surface 135 when an endoscope shaft 320 is engaged in the channel, thereby preventing the slide-on channel adapter from sliding off the handle when the endoscope is engaged. Mechanisms other than those illustrated may be utilized to removably couple and/or secure channel 130 to the body of handle 120. One advantage of removably coupling a channel 130 or other attachment adapter to the body of handle 120 is that different types of attachment channels or adapters may be coupled to the handle, enabling the one-handed use of device 100 with different types of endoscope shafts or even other instruments, depending on the adapter that is used. In alternative implementations, the channel 130 is fixed to/integrated on the body of handle 120.

As also illustrated in this example, a distal end of elevator 110 includes a clip 115 configured to secure a distal end of endoscope shaft 320.

Other endoscope attachment mechanisms may be incorporated into elevator 110 and/or handle 120. For example, handle 120 may couple to a proximal end of endoscope shaft 320 utilizing a magnetic attachment mechanism, a snap on attachment mechanism, a top-down ratchet mechanism, an insert ratchet mechanism, an insert twist mechanism, or other attachment mechanism as further described in U.S. Pat. No. 10,512,391, incorporated herein by reference in its entirety. Elevator 110 may couple to the distal end of endoscope shaft 320 utilizing a magnetic attachment mechanism, loop(s), clip(s), elongated tube(s), a removable insert, or other attachment mechanism as further described in U.S. Pat. No. 10,512,391. The elevator 110 and/or handle 120 may also utilize one or more of the endoscope attachment mechanisms described in U.S. patent application Ser. No. 17/503,044, filed Oct. 15, 2021, titled "Endoscope with Integrated Attachment Mechanisms and Methods of Use", and incorporated herein by reference in its entirety. As such, it should be noted that the disclosure is not limited to the specific endoscope attachment mechanisms described and illustrated herein for removably coupling endoscope 300, and that other mechanisms for removably coupling the endoscope 300 are contemplated. Additionally, although an endoscope 300 having a flexible (e.g., bendable) shaft 320 that is part rigid and part flexible (hybrid) is illustrated, in other implementations the assembly may be adapted to receive an endoscope having an entirely rigid shaft or entirely flexible shaft.

Although the figures depict the retractable syringe device 100 including structures (e.g., clip 115 and channel 130) for removably coupling an endoscope 300 to device 100, in other implementations endoscope mounting structure(s) may be omitted from device 100. In such implementations, an endoscope may be separately held and manipulated by an operator. For example, the operator may hold retractable syringe device 100 in one hand and an endoscope 300 in the other hand.

Although the disclosure has been described in the context of a retractable syringe device including an elevator with a channel from which a syringe needle withdraws and extends, it is envisioned that the retractable syringe device could be used with other medical instruments besides an elevator. Similar to the operation of the elevator, these other instruments could be used to manipulate an anatomical structure such as tissue or body fluids in a manner that facilitates endoscopic visualization for tissue injection. For example, a protected channel for retracting or extending a syringe needle could be incorporated into instruments such as a lumen tip of a flexible endoscope, a biopsy forceps, an articulating forceps, a tip of a balloon cannula, a flexible cannula, a rigid cannula, an articulating cannula, a suction device, a cautery, a coblation wand, or a plasma wand. In such implementations, the handle 120 of the retractable syringe device could be adapted (e.g., by modifying the distal end of the handle) to removably couple to such other instruments, or to be integrated into such other instruments.

It is also envisioned that the needle itself could be attached to a cautery that is either separate from or incorporated into the handle 120.

It is further envisioned that embodiments could be implemented whereby multiple needles could be withdrawn or extended, independently or in unison, from one instrument or multiple instruments.

Embodiments described herein may be used with a variety of different syringe types other than what is depicted in the figures. Depending on the medical application and shape of the handle, characteristics of the syringe may vary, including its volume, length, shape, plunger mechanism, needle attachment mechanism, and/or proximal arm configuration. For example, the syringe volume may vary from 1 cc to 60 cc depending on the medical application. In some implementations, the syringe may itself incorporate a fixed or removable endoscope attachment mechanism such as a channel, a magnet, a rail/track mechanism, a clip a tube, an adhesive, etc.

Embodiments described herein may also be used with a variety of different needle types other than what depicted in the figures. The needle may be large bore, small bore, rigid, flexible, reinforced, reusable, disposable, straight, or pre-bent to conform to a particular application or instrument type. The needle may be inserted proximally into an instrument as described above with respect to the elevator, or side loaded, either partially or completely through a channel or gap in the side of an instrument shaft.

Embodiments described herein may also be used with a variety of different handles other than what is depicted in the figures. The handle may vary in size, length, or width depending on the syringe size required. Syringes could attach to the handle in-line with the needle, syringe, and endoscope, offset from needle, syringe, and/or endoscope, contained within a pistol grip handle, actuated in an over hand manner, motorized, automated, incorporated with sound or vibratory reinforced volumetric dispensing, etc. Various handle configurations and finger slots/rings to allow for ergonomic holding and stabilization of the device are envisioned. In some implementations, depending on the length and volume of the syringe required, the handle without attached elevator could vary in length between 5 cm and 25 cm, and vary in width between 0.5 cm and 6 cm. Instruments containing the channels to house the needles could likewise be of different lengths and configurations.

Although described above in terms of various example implementations, it should be understood that the various features, aspects and functionality described in one or more of the individual implementations are not limited in their applicability to the particular implementation with which they are described, but instead can be applied, alone or in various combinations, to one or more of the other implementations of the application, whether or not such implementations are described and whether or not such features are presented as being a part of a described implementation.

Thus, the breadth and scope of the present application should not be limited by any of the above-described example implementations.

To the extent applicable, the terms "first," "second," "third," etc. herein are merely employed to show the respective objects described by these terms as separate entities and are not meant to connote a sense of chronological order, unless stated explicitly otherwise herein.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide some instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

While various implementations of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Additionally, with regard to flow diagrams, operational descriptions and method claims, the order in which the steps are presented herein shall not mandate that various implementations be implemented to perform the recited functionality in the same order unless the context dictates otherwise.

What is claimed is:

1. A retractable syringe device, comprising:
  a handle comprising:
    a handgrip; and
    a hollow body for inserting a syringe received through an opening of the handle such that a reservoir of the syringe for holding fluid and a distal end of the syringe for delivering the fluid longitudinally extend through the hollow body, the hollow body including a syringe actuator that holds the syringe in the hollow body and moves the syringe, including the reservoir and the distal end, between a distal position in the hollow body and a proximal position in the hollow body, wherein the syringe actuator is configured to hold the syringe in place in the distal position, the syringe actuator comprising:
      a cam; and
      a pawl, the pawl configured to be engaged with the cam by pushing the syringe forward a first time in the hollow body until the syringe is in the distal position, and the pawl configured to be disengaged from the cam by pushing the syringe forward a second time in the hollow body when the syringe is in the distal position, thereby causing the syringe to retract toward the proximal position; and
  a surgical elevator distally extending from the handle, the surgical elevator including:
    a blunt curved tip that is rigid or semi-rigid, the blunt curved tip configured to displace an anatomical structure to facilitate visualization of an injection site by an endoscope;
    a channel extending through the surgical elevator, the channel configured to receive an injection needle directly coupled to the distal end of the syringe, wherein moving the syringe, including the reservoir and the distal end of the syringe, from the proximal position to the distal position in the hollow body causes a distal end of the injection needle to distally extend to outside the channel, and moving the syringe, including the reservoir and the distal end of the syringe, from the distal position to the proximal position in the hollow body causes the distal end of the injection needle to be retracted into the channel; and
    a rotatable dial that rotates the surgical elevator relative to the handle.

2. The retractable syringe device of claim 1, wherein the syringe actuator further comprises a spring.

3. The retractable syringe device of claim 2, wherein:
  the syringe actuator further comprises a sleeve configured to hold the syringe, including the reservoir of the syringe, in the hollow body; and
  the spring is configured to provide tension to retract the sleeve.

4. The retractable syringe device of claim 1, wherein the handle further comprises a syringe locker that prevents removal of the syringe, including the reservoir of the syringe, from inside the hollow body of the handle.

5. The retractable syringe device of claim 4, wherein the syringe locker comprises a twist lock mechanism.

6. The retractable syringe device of claim 4, wherein the syringe locker comprises a grip for holding a lip of the syringe distal to a plunger of the syringe and proximal to the reservoir of the syringe.

7. The retractable syringe device of claim 1, wherein the handle further comprises a first structure for removably coupling to a proximal end of a shaft of the endoscope.

8. The retractable syringe device of claim 7, wherein the first structure for removably coupling to the proximal end of the shaft of the endoscope comprises a magnetic attachment, a snap on attachment, a top-down ratchet attachment, an insert ratchet attachment, or an insert twist attachment.

9. The retractable syringe device of claim 7, wherein the surgical elevator further comprises a second structure for removably coupling to a distal end of the shaft of the endoscope.

10. The retractable syringe device of claim 9, wherein the second structure for removably coupling to the distal end of the shaft of the endoscope comprises: a magnetic attachment, a loop, a clip, an elongated tube, or a removable insert.

11. A retractable syringe device, comprising:
  a handle comprising:

a hollow body for receiving a syringe through an opening of the handle, the hollow body including a syringe actuator that moves the syringe between a distal position and a proximal position; and a first structure for removably coupling to a proximal end of a shaft of an endoscope, wherein: the handle comprises an elevated surface; the first structure comprises an open channel configured to be removably coupled to the elevated surface; and the open channel comprises a depressible tab configured to be depressed into an opening of the elevated surface when the proximal end of the shaft of the endoscope is removably coupled to the first structure; and an instrument distally extending from the handle, the instrument including a channel extending through the instrument, the channel configured to receive a needle coupled to the syringe, wherein when the syringe is in the distal position, a distal end of the needle distally extends from the instrument, and when the syringe is in the proximal position, the distal end of the needle is retracted into the channel.

12. The retractable syringe device of claim 1, wherein the handle opening is at a proximal end of the handle.

13. A retractable syringe device assembly, comprising:
a syringe including a reservoir for storing fluid and a distal end for delivering the fluid;
an injection needle to directly couple to the distal end of the syringe and inject the fluid at an anatomical structure;
a handle comprising a handgrip, and a hollow body for inserting the syringe through an opening of the handle such that the reservoir and the distal end longitudinally extend through the hollow body, the hollow body including a syringe actuator that holds the syringe in the hollow body and moves the syringe, including the reservoir and the distal end, between a distal position in the hollow body and a proximal position in the hollow body, wherein the syringe actuator is configured to hold the syringe in place in the distal position, the syringe actuator comprising:
a cam; and
a pawl, the pawl configured to be engaged with the cam by pushing the syringe forward a first time in the hollow body until the syringe is in the distal position, and the pawl configured to be disengaged from the cam by pushing the syringe forward a second time in the hollow body while the syringe is in the distal position, thereby causing the syringe to retract toward the proximal position; and
a surgical elevator distally extending from the handle, the surgical elevator including:
a blunt curved tip that is rigid or semi-rigid, the blunt curved tip configured to displace the anatomical structure to facilitate visualization of an injection site by an endoscope;
a channel extending through the surgical elevator, the channel configured to receive the injection needle, wherein moving the syringe, including the reservoir and the distal end of the syringe, from the proximal position to the distal position in the hollow body causes a distal end of the injection needle to distally extend to outside the channel, and moving the syringe, including the reservoir and the distal end of the syringe, from the distal position to the proximal position in the hollow body causes the distal end of the injection needle to be retracted into the channel; and
a rotatable dial that rotates the surgical elevator relative to the handle.

14. The retractable syringe device assembly of claim 13, wherein the handle further comprises a structure for removably coupling to a proximal end of a shaft of the endoscope.

15. The retractable syringe device assembly of claim 14, further comprising the endoscope.

16. The retractable syringe device assembly of claim 13, wherein the syringe actuator further comprises:
a sleeve configured to hold the syringe, including the reservoir of the syringe, in the hollow body; and
a spring configured to provide tension to retract the sleeve.

17. The retractable syringe device of claim 1, wherein the surgical elevator is removably coupled to a distal end of the handle.

* * * * *